(12) United States Patent
Kaiser et al.

(10) Patent No.: US 6,383,505 B1
(45) Date of Patent: May 7, 2002

(54) FAST-ACTING ANTIMICROBIAL LOTION WITH ENHANCED EFFICACY

(75) Inventors: Nancy E. Kaiser, Pontoon Beach, IL (US); Denise K. Pretzer, Webster Groves; Kevin A. Tibbs, St. Louis, both of MO (US)

(73) Assignee: Steris Inc, Temecula, CA (US)

( * ) Notice: Subject to any disclaimer, the term of this patent is extended or adjusted under 35 U.S.C. 154(b) by 0 days.

(21) Appl. No.: 09/710,804

(22) Filed: Nov. 9, 2000

(51) Int. Cl.[7] .......................... A01N 25/24; A61K 7/00; A61K 31/14
(52) U.S. Cl. ..................... 424/407; 514/643; 424/405
(58) Field of Search .................. 514/643; 424/405, 424/407

(56) References Cited

U.S. PATENT DOCUMENTS

| | | |
|---|---|---|
| 1,540,793 A | 9/1925 | Maloney |
| 3,893,843 A | 7/1975 | Fry et al. |
| 3,950,554 A | 4/1976 | Prince |
| 4,067,967 A | 1/1978 | Prince |
| 4,341,677 A * | 7/1982 | Tanosauskas |
| 4,390,442 A | 6/1983 | Quick |
| 4,456,543 A | 6/1984 | Owens |
| 4,587,266 A | 5/1986 | Verdicchio |
| 4,748,158 A | 5/1988 | Biermann et al. |
| 4,879,274 A | 11/1989 | Kamiya et al. |
| 4,919,837 A | 4/1990 | Gluck |
| 4,923,685 A | 5/1990 | Wuelknitz et al. |
| 4,942,029 A | 7/1990 | Scheps |
| 5,008,038 A | 4/1991 | Merianos et al. |
| 5,017,617 A | 5/1991 | Kihara et al. |
| 5,035,752 A | 7/1991 | Tanaka et al. |
| 5,120,512 A | 6/1992 | Masuda |
| 5,164,107 A | 11/1992 | Kahn et al. |
| 5,232,691 A | 8/1993 | Lemole |
| 5,266,598 A | 11/1993 | Ninomiya et al. |
| 5,368,850 A * | 11/1994 | Cauwet et al. |
| 5,478,864 A | 12/1995 | Nishihara et al. |
| 5,529,770 A | 6/1996 | McKinzie et al. |
| 5,635,469 A | 6/1997 | Fowler et al. |
| 5,719,113 A | 2/1998 | Fendler et al. |
| 5,763,412 A | 6/1998 | Kahn et al. |
| 5,776,430 A | 7/1998 | Osborne et al. |
| 5,830,488 A | 11/1998 | Suzuki et al. |
| 5,885,948 A | 3/1999 | Glenn, Jr. et al. |
| 5,906,808 A | 5/1999 | Osborne et al. |
| 5,908,865 A | 6/1999 | Doi et al. |
| 5,912,002 A | 6/1999 | Grieveson et al. |
| 5,922,313 A | 7/1999 | Steward et al. |
| 5,922,693 A | 7/1999 | Oldenhove |
| 5,948,416 A | 9/1999 | Wagner et al. |
| 5,951,991 A | 9/1999 | Wagner et al. |
| 5,951,993 A | 9/1999 | Scholz et al. |
| 5,972,361 A | 10/1999 | Fowler et al. |
| 5,980,878 A | 11/1999 | Torgerson et al. |
| 5,980,925 A | 11/1999 | Jampani et al. |
| 5,989,536 A | 11/1999 | Deckner et al. |
| 5,997,893 A | 12/1999 | Jampani et al. |
| 6,017,516 A | 1/2000 | Mody et al. |
| 6,017,520 A | 1/2000 | Synodis et al. |
| 6,022,551 A | 2/2000 | Jampani et al. |
| 6,028,113 A | 2/2000 | Scepanski |
| 6,045,817 A | 4/2000 | Ananthapadmanabhan et al. |
| 6,046,238 A | 4/2000 | Yu et al. |
| 6,063,397 A | 5/2000 | Fowler et al. |
| 6,066,602 A | 5/2000 | Khan et al. |
| 6,066,606 A | 5/2000 | Lu et al. |
| 6,066,674 A | 5/2000 | Hioki et al. |
| 6,071,866 A | 6/2000 | Fujiwara et al. |
| 6,080,707 A | 6/2000 | Glenn, Jr. et al. |
| 6,080,708 A | 6/2000 | Glenn, Jr. et al. |
| 6,083,517 A | 6/2000 | Ananthapadmanabhan et al. |
| 6,090,395 A | 7/2000 | Asmus et al. |
| 6,107,261 A | 8/2000 | Taylor et al. |
| 6,121,224 A | 9/2000 | Fonsny et al. |
| 6,136,765 A | 10/2000 | Glenn, Jr. et al. |

\* cited by examiner

*Primary Examiner*—William R. A. Jarvis
*Assistant Examiner*—Vickie Kim
(74) *Attorney, Agent, or Firm*—Fay, Sharpe, Fagan, Minnich & McKee, LLP

(57) ABSTRACT

An antimicrobial lotion for topical use comprises an oil-in-water emulsion with a dispersant of emollient droplets in an oil phase and an antimicrobial agent in a water phase. The emollients moisturize the skin. Antimicrobial agents have a more rapid antimicrobial effect in an aqueous solution than in the oil phase. A combination of anionic and nonanionic surfactants stabilize the emulsion and maintain a cationic antimicrobial agent primarily in the water phase. The resulting lotion is gentle on the skin while providing more rapid antimicrobial effect than conventional lotions. With longer lasting antimicrobial agents, such as chlorhexidene, the lotion is rubbed into the skin and left on to continue moisturizing and killing microbes for up to 12 hours.

27 Claims, No Drawings

FAST-ACTING ANTIMICROBIAL LOTION WITH ENHANCED EFFICACY

BACKGROUND OF THE INVENTION

The present invention relates to the antimicrobial arts. It finds particular application in conjunction with the reduction of microorganisms on and moisturization of the skin of health care personnel and will be described with particular reference thereto. It should be appreciated, however, that the invention is also applicable outside the medical area, such as a skin conditioning lotion for workers in the food preparation industry, in home health care, or in other areas where skin disinfection and moisturization is desired.

The chemical control of bacteria and viruses is assuming increasing importance in the hospital and medical fields. A wide variety of topical compositions for treatment of the skin are available, including moisturizers, anti-acne compositions, sunscreens, topical anesthetics, artificial tanning compositions, skin lightening compositions, anti-wrinkle compositions, and the like, often in the form of lotions. The most common lotions use anionic, or negatively charged, emulsifiers to stabilize the composition. These lotions have no antimicrobial activity and are used for moisturization only. Nonionic emulsifier-based lotions can also be made, however these tend to be low viscosity fluids.

Lotions are also available which are compatible with an antimicrobial residue left behind on the skin after washing or rinsing with an antimicrobial-containing product. However, these antimicrobial wash products are not themselves moisturizing and are therefore used prior to separate moisturizing product. The antimicrobial wash product is not left on the skin but is washed off prior to the application of the moisturizers. Such antimicrobial wash products would be harsh to the skin if utilized repeatedly in leave-on applications.

Lotions have been developed which provide antimicrobial activity to destroy microorganisms, such as bacteria, on the surface of the skin, while also providing a moisturizing function. Several leave-on products have been developed including those which contain triclosan as the active ingredient. These tend to be relatively ineffective at reducing the antimicrobial population on the skin.

Alcohol-containing products, which include chlorhexidine, are also known. Such compositions use both alcohol and chlorhexidine for quick and persistent activity. However, the alcohol tends to be drying to the skin. Those formulas which also contain emollients to counteract this drying effect tend have a reduced moisturizing effect on the dry skin. Additionally, these products are not actually lotions (stable oil-in-water emulsions) but function as a gel in which the antimicrobial agent is dispersed throughout the composition.

The present invention provides a new and improved skin care composition and method of use which overcomes the above-referenced problems and others.

SUMMARY OF THE INVENTION

In accordance with one aspect of the present invention, an oil-in-water emulsion for antimicrobial skin treatment is provided. The composition includes a nonionic emulsifier, an anionic emulsifier, a cationic antimicrobial agent, a carrier oil, and water.

In accordance with another aspect of the present invention, a fast acting antimicrobial lotion is provided. The lotion includes, as a percent by weight, 0.25–8.0% of a nonionic emulsifier, 0.1–2.0% of an anionic emulsifier, 0.5–10.0% of a thickener, 0–15.0 % of a humectant, 0.02–5.0% of a skin conditioner, 2.0–20.0% of an oil, 0.25–5% of a cationic antimicrobial agent, and water.

One advantage of the present invention is that the skin is microbially decontaminated and moisturized in a single application.

Another advantage of the present invention is that the composition is fast-acting.

Yet another advantage of the present invention is that it avoids the use of substantial quantities of alcohol in the composition, which tends to be drying to the skin.

Yet another advantage of the present invention is that it provides equivalent antimicrobial activity to conventional cationic antimicrobial containing wash products at substantially lower concentrations of the active ingredient.

Another advantage of the present invention is that it enables the viscosity of the composition to be increased to a level which retains the antimicrobial on the skin for an extended period of time.

Yet another advantage of the present invention is that the composition need not be removed from the skin as it is moisturizing and nondrying.

Still further advantages of the present invention will become apparent to those of ordinary skill in the art upon reading and understanding the following detailed description of the preferred embodiments.

DETAILED DESCRIPTION OF THE PREFERRED EMBODIMENTS

A skin care composition which provides antimicrobial activity while moisturizing the skin is provided. The composition may be used in place of hand washing, as an adjunct to hand washing, as a surgical scrub, or as a surgical preoperative skin preparation. The composition is preferably used as a leave-on composition, which is applied to the skin and left in place to provide both immediate and long term antimicrobial activity and moisturizing functions. While use of the composition is described with reference to application to skin, particularly human skin, the composition may also be used for treatment of hair, scalp, and on animals.

By antimicrobial activity, it is meant that the composition reduces the number of viable microorganisms on the skin, primarily by inactivating or killing the microorganisms, rather than by physically removing them.

The skin care composition comprises an oil-in-water emulsion which includes an antimicrobial agent, preferably a cationic antimicrobial agent. By oil-in-water emulsion, it is meant that the composition is formulated to have a discontinuous oil phase that is dispersed in a water, i.e., the aqueous phase. Specifically, a fine dispersion of oil phase droplets is held in the surrounding water phase by suitable emulsifiers. In the present case, the formulation maintains the antimicrobial agent primarily in the external phase (water) rather than in the internal phase (oil). This allows the antimicrobial to be more readily available and increases the rate of kill of microorganisms. This is in contrast to prior compositions, in which a large portion of the active is found in the internal phase, where it is unavailable for immediate activity on the skin.

The oil in water emulsion comprises an aqueous phase at from about 40% to about 95% by weight of the total composition. Preferably, the compositions includes from about 60 to about 80% by weight of an aqueous phase, in which the oil phase is dispersed.

Emulsifier System

The composition includes a combination of at least one anionic emulsifier and at least one nonionic emulsifier, the nonionic emulsifier(s) preferably being at a higher concentration than the anionic emulsifier(s). It has been found that a combination of anionic and nonionic emulsifiers provides better stability to the emulsion, while simultaneously providing unexpectedly better antimicrobial activity. While a single emulsifier may be used, the microbial activity and physical stability are generally significantly reduced.

The preferred emulsifiers are surfactants which are non-foaming, and thus differ from the conventional high-foaming surfactants used in wash-off compositions. Additionally the concentration of the emulsifiers is less than that used in wash-off compositions, which typically use significantly greater than 5% total surfactants. Specifically, the emulsifiers of the present composition are preferably used in a sufficient amount to just coat the surface area of all of the oil droplets. However, if too much emulsifier is used, it tends to move into the water phase, where it binds and micellizes the chlorhexidine gluconate or other antimicrobial agent, reducing its antimicrobial activity. If too little emulsifier is used, the oil droplets are not fully coated and the chlorhexidine gluconate tends to attach to the surfaces of the oil droplets, also leading to reduced antimicrobial activity. Consequently, the optimal amount of emulsifier used depends on the total amount of oil and type of oil used in the composition. The optimal amount can be determined by efficacy studies in which the concentration of emulsifier is varied and the antimicrobial efficacy is measured. A plot of efficacy against emulsifier concentration shows a peak at the optimal concentration. When cyclomethicone or similar simethicone is used as the oil at a concentration of about 5–12 weight percent, the total emulsifier content is preferably less than about 5 wt. %, more preferably between 1 and 5%, i.e., an oil to surfactant ratio of about 2.5:1 or higher.

To avoid micellization of the antimicrobial agent, it is preferable to add the antimicrobial agent after forming the oil-in-water emulsion.

Nonionic Emulsifier

It has been found that by using an appropriate amount of a nonionic emulsifier, the cationic antimicrobial agent can be maintained primarily in the water phase. This makes the antimicrobial more available, i.e., more effective at decontaminating the skin surface in a reduced time frame. The nonionic emulsifier is preferably present in the composition at a concentration of from 0.25%–8% by weight, more preferably, from about 1% to about 5% by weight.

Exemplary nonionic emulsifiers include polyoxyethylene alcohols and glycol fatty acid esters with an ethoxylation range of 2–100 mols, suitable fatty alcohol groups including lauryl, cetyl, cetearyl, oleyl, and tridecyl. Examples of glycol fatty acid esters include ceteareth-10, laureth-4, and the like. Other nonionic emulsifiers include fatty acid esters of sorbitan and polyoxyethylene sorbitan, polyoxyethylene fatty acid esters, quaternary amine salts of fatty acids, phospholipid complexes/emulsifiers, polyol fatty acid esters, and polymeric surfactants. Examples include Hypermer's, a polymeric surfactant obtained from ICI America, PEG-X soya sterol oil and the diethanolamine salt of cetyl phosphate. The nonionic emulsifier may be a combination of two or more emulsifiers.

Preferred nonionic emulsifiers are $C_{12}$–$C_{22}$ ethoxylated fatty alcohols, particularly glycol fatty acid esters such as stearyl ethers characterized by the CTFA designation as Steareth X, where X is from 2 to 100 mols ethoxylation. Examples include Steareth-2, Steareth-10, Steareth 21, Steareth-100. A combination of two or more of the Steareth compounds is particularly preferred, to provide a hydrophobic lipophilic balance (HLB) which maintains the oil-in-water emulsion. A suitable HLB number for the system is from about 10–20, more preferably 10–15, most preferably, about 12.5. Of course, other components of the composition, such as cyclomethicone, also contribute to the overall desired HLB.

For example, a combination of Steareth $X_1$ and Steareth $X_2$ may be used, where $X_1$ is from 2 to 10 mols ethoxylation, and $X_2$ is from 11 to 100 moles ethoxylation.

Anionic Emulsifier

The anionic emulsifier is preferably present in the composition at a concentration of 0.1–2.0% by weight, more preferably, at a concentration of 0.1–0.75% by weight.

Suitable anionic emulsifiers are of the general formula $RCO(OCHCH_3CO)_n$ $O^-$ $X^+$, where R is a long chain aliphatic group, such as caproyl, lauroyl, stearoyl, n is an integer, principally 1 or 2, and X is a cation (such as $Na^+$, $Ca^+$, $K^+$, $NH_4^+$, or alkanolamine, e.g., triethanolamine). The alkyl group of the fatty acid preferably has from 6–22 carbons, such as caproyl, isostearoyl, cocoyl, hydroxystearoyl, behenoyl, stearoyl, and the like. Exemplary anionic emulsifiers of this type include cationic salts of esters of lactyl lactylates, such as potassium, sodium, triethanolamine, and calcium salts of lauroyl lactylate, cocoyl lactylate, stearoyl lactylate, and caproyl lactylate.

Preferred emulsifiers are low foaming. A particularly preferred anionic emulsifier is a salt of lauroyl lactylate, such as sodium lauroyl lactylate.

The Water Phase

Antimicrobial Agent

The composition includes a safe and effective amount of at least one active antimicrobial ingredient. The term "safe and effective amount," as used herein, means an amount which is safe for use on human skin, and which is sufficient to bring about a desired level of microbial decontamination. This level may be complete sterilization, or some lesser level of microbial decontamination, such as disinfection or sanitization. The exact amount will depend on the agent selected, the desired level of antimicrobial activity, the amount of the composition to be applied, the exposure time, viscosity, and other factors.

The composition preferably includes a cationic antimicrobial as the active ingredient. Suitable cationic antimicrobials include salts of chlorhexidine, such as chlorhexidene digluconate, chlorhexidene acetate, chlorhexidene isethionate, chlorhexidene hydrochloride. Other cationic antimicrobials may also be used, such as benzalkonium chloride, benzethonium chloride, polyhexamethylene biguanide, cetyl puridium chloride, methyl and benzothonium chloride.

Salts of chlorhexidine, in particular, chlorhexidene digluconate, are particularly preferred antimicrobials. A combination of cationic antimicrobials may be used. Cationic antimicrobials in the past have not been used in combination with anionic surfactants as they are generally considered to be incompatible.

The cationic antimicrobial agent is present in a sufficient amount to microbially decontaminate the skin of the user. For salts of chlorhexidine, such as chlorhexidine gluconate, a preferred concentration is from 0.25 to 5% by weight, more preferably, from about 0.5 to about 4% by weight of the composition.

Other antimicrobials may also be used, alone or in age combination with a cationic antimicrobial agent as previously described. These include halogenated phenolic compounds, such as 2,4,4',-trichloro-2-hydroxy diphenyl ether (Triclosan); parachlorometa xylenol (PCMX); and short chain alcohols, such as ethanol, propanol, and the like. For example, a combination of chlorhexidine gluconate and ethanol may be used. However, the alcohol is preferably at a low concentration (below about 10% by weight of the composition and, more preferably, below 5% by weight) so that it does not cause undue drying of the skin.

Humectants (Cosolvents)

A humectant is preferably present in the composition at a concentration of from 2–15% by weight, more preferably, from 2–10% by weight. The humectant is a water soluble component, i.e., it is primarily present in the aqueous phase. The humectant used herein provide stability to the water phase, however it may also provide other functions, such as promotion of water retention by the skin or hair, emolliency, and other moisturizing or conditioning functions.

Suitable humectants are polyhydric alcohols, such as $C_3$–$C_6$ diols and triols, and polyethylene glycols. These act as cosolvents and help to stabilize the water phase. Examples include propylene glycol, dipropyleneglycol, hexylene glycol, 1,4-dihydroxyhexane, 1,2,6-hexanetriol, sorbitol, butylene glycol, propanediols, such as methyl propane diol, dipropylene glycol, triethylene glycol, glycerin (glycerol), polyethylene glycols, ethoxydiglycol, polyethylene sorbitol, and combinations thereof. Other humectants include glycolic acid, glycolate salts, lactate salts, lactic acid, sodium pyrrolidone carboxylic acid, hyaluronic acid, chitin, and the like.

Particularly preferred as humectants are propylene glycol and glycerin. These have been found to have a positive effect on both the moisturizing function and the antimicrobial activity of the composition.

Other cosolvents include alcohols, such as ethanol, n-propanol, and isopropanol; triglycerides; ethyl acetate; acetone; triacetin; and combinations of these.

Skin Conditioner/Emollient

The composition may also include a skin conditioner/emollient at a concentration of from 0.02–5% by weight, more preferably, from about 0.05 to about 2% by weight. Exact levels of emollient will depend upon the material chosen with consideration being given to the effects upon the composition.

Emollients in skin and personal care compositions are materials which are used to replace or add lipids and natural oils in the skin or hair. The emollient materials help to provide a skin conditioning benefit, moisturizing the skin by depositing on the skin or hair during the application process.

Suitable skin conditioners include quaternary ammonium salts of acrylamide and dimethyl diallyl ammonium chloride (DIMDAC) polymers, such as Polyquaternium-6, Polyquaternium-7 and Polyquaternium-10. Also useful are nonvolatile silicones, such as polydialkylsiloxanes, polydiarylsiloxanes, and polydialkarylsiloxanes. Polyalkyl siloxanes have the general formula $R^3SiO[R^2SiO]_xSiR^3$, where $R^2$ and $R^3$ independently are an alkyl group, such as methyl or ethyl, and x is an integer up to about 500, chosen to achieve the desired molecular weight. Commercially available polyalkylsiloxanes include polydimethylsiloxanes, also known as dimethicones. Useful polyalkylaryl siloxanes include polymethylphenyl siloxanes.

Also useful are dimethiconols, which are hydroxy-terminated dialkyl silicones, such as dimethyl silicones. These materials may be represented by the general formulae $R^4SiO[R^5_2SiO]_xSiR^6OH$ and $HOR^7SiO[R^8SiO]_xSiR^9OH$, wherein $R^4$–$R^9$ are independently an alkyl group, preferably methyl or ethyl; and x is an integer up to about 500, chosen to achieve the desired molecular weight.

Other useful skin conditioners are silicone polyethers; alkyl methyl silicones; $C_8$–$C_{30}$ alkyl esters of $C_8$–$C_{30}$ carboxylic acids; $C_1$–$C_6$ diol monoesters and diesters of $C_8$–$C_{30}$ carboxylic acids; cholesterol esters of $C_8$–$C_{30}$ carboxylic acids; monoglycerides, diglycerides, and triglycerides of $C_8$–$C_{30}$ carboxylic acids; polyethylene glycol derivatives of vegetable glyceride; hydrocarbon oils or waxes, and silicone gum/resin blends. Examples of these materials include diisopropyl adipate, isopropyl myristate, isopropyl palmitate, palm kernel glyceride, caprylic glyceride, capric glyceride, glyceryl cocoate, $C_{12}$–$C_{15}$ alkyl benzoates; PPG-15 stearyl ether benzoates; dipropylene glycol benzoate; cetyl esters; chitosan; cetyl lactate; PEG-60 corn glyceride; PEG-45 palm kernel glyceride; pentaerythrityl tetraisostearate; hydrogenated polybutenes; polyisobutene; aloe vera (which also serves as a humectant); vitamin E; mucopolysaccharides; (hydrogenated) 1-decene homopolymers; steroid alcohols; and combinations thereof. Other useful skin conditioners include sorbitan laurate, lanolin, lanolin esters, alkoxylated and/or polyoxylated $C_3$–$C_6$ diols and triols, ethoxylated and propoxylated sugars, such as mannitol, and the like.

Among the skin conditioners preferred are Polyquaternium salts, dimethicone, dimethiconol, cetyl esters, glyceryl esters of fatty acids, particularly palm kernel glyceride, caprylic glyceride, and capric glyceride, glyceryl cocoate, $C_{12}$–$C_{15}$ alkyl benzoates, dipropylene glycol benzoate, PPG 15 stearyl ether benzoate, chitosan, and cetyl lactate. Polyquaternium salts, such as Polyquaternium-7, are particularly preferred skin conditioners. They may be purchased from Calgon Chemical as 8% or 40% solutions.

Thickener

The water phase is preferably thickened with a thickening agent to provide the composition with a suitable viscosity to keep the composition in contact with the skin for an extended period. The thickening agent is one which is compatible with cationic actives, such as chlorhexidine gluconate.

Suitable thickeners (which in some cases may also contribute some emulsification properties) include alcohols, such as cetyl, stearyl, cetostearyl, caprylic, myristyl, decyl, lauryl, and oleyl alcohol; emulsifying waxes, such as Emulsifying Wax NF (a cetostearyl alcohol plus polyoxyethylene derivative of a fatty acid ester of sorbitan; fatty acid esters, such as monoesters of a fatty acid and glycerine; and mono or di esters of fatty acids and glycol. Examples of fatty acid esters include glyceryl stearate, glyceryl oleate, glyceryl palmitate. Examples of mono and di esters of fatty acids and glycol include glycol stearate, glycol dilaurate, glycol hydroxystearate, and glycol distearate.

Polymeric thickeners may also be used, such as hydroxymethyl cellulose, hydroxyethyl cellulose, cetyl hydroxymethyl cellulose, guar gum, and the like. Polyethylene glycols may also be used, preferably those having a weight average molecular weight ($M_W$) range of from about 400 to about 4000.

Cetyl alcohol is particularly preferred thickener since it also acts as an emulsifier and an emollient.

The concentration of the thickener depends on the selected thickener and the desired viscosity. A preferred viscosity is at least about 1000 cps. In the case of cetyl alcohol, the concentration is preferably from 0.5–10%, more preferably, from about 0.5 to about 6% by weight of the composition.

Water

The balance of the aqueous phase is water. The composition includes from about 35% to about 90% water, more preferably, from about 60% to about 85% water. The exact level of water depends on the desired levels of the various components and any other additives employed.

The Oil Phase Carrier

The oil phase comprises one or more oils or oil phase component (all generally referred to herein as "carrier oils"), which acts as a carrier for the oil phase.

The carrier oil is present in the composition preferably at a concentration of 2–20% by weight, more preferably, from about 5 to 12% by weight.

Suitable carrier oils include volatile silicones, such as cyclomethicone, dimethicone; siloxanes, such as tetra, penta, or hexa cyclosiloxane, hexamethyl disiloxane, and octyltrisiloxane.

Preferred are volatile silicones, such as cyclomethicone. These silicones act as an emollient, in addition to a carrier, and provide lubricity to the composition. Cyclomethicone is a particularly preferred carrier. It is a non-greasy volatile silicone, which dissipates when rubbed in to the skin.

The Preferred Compositions

A preferred composition includes:

| Component | % by weight of active indredient |
| --- | --- |
| Nonionic Emulsifier | 0.25–8.0 |
| Anionic Emulsifier | 0.1–2.0 |
| Thickener | 0.5–10.0 |
| Humectant | 0–15.0 |
| Skin Conditioner | 0.02–5.0 |
| Carrier | 2.0–20.0 |
| Antimicrobial Agent | 0.25–5 |

A particular preferred composition includes:

| Component | % by weight of active ingredient |
| --- | --- |
| Nonionic Emulsifier (Two or more Steareth compounds) | 1.0–5.0 |
| Anionic Emulsifier (lactylate) | 0.1–0.75 |
| Thickener (fatty alcohol) | 0.5–6.0 |
| Humectant (polyhydric alcohol) | 2.0–10.0 |
| Skin Conditioner (Polyquaternium) | 0.02–2.0 |
| Carrier (cyclomethicone) | 5.0–12.0 |
| Antimicrobial Agent (chlorhexidine digluconate) | 0.5–4.0 |

The chlorhexidine gluconate:nonionic emulsifier ratio is from about 1:5 to about 1:1, the optimal amount depending on the amount of the internal (oil) phase.

Other additives

The composition of the present invention can also comprise a wide range of other additional components. The *CTFA Cosmetic Ingredient Handbook*, Second Edition, 1992, describes a wide variety of nonlimiting cosmetic and pharmaceutical ingredients commonly used in the skin care industry, which are suitable for use in the compositions of the present invention. Examples of functional classes of additional components include: absorbents, abrasives, anti-acne agents, anticaking agents, antifoaming agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, plasticizers, preservatives, propellants, reducing agents, skin protectants, solvents, suspending agents (nonsurfactant), ultraviolet light absorbers, and viscosity increasing agents (aqueous and nonaqueous). Examples of other functional classes of materials useful herein that are well known to one of ordinary skill in the art include emulsifiers, solubilizing agents, and sequestrants, and the like.

Nonlimiting examples of these additional components cited in the *CTFA Cosmetic Ingredient Handbook*, as well as other materials useful herein, include the following: vitamins and derivatives thereof [e.g., vitamin C, tocopherol, tocopherol acetate, and the like]; anti-oxidants; polyethyleneglycols and polypropyleneglycols; preservatives for maintaining the antimicrobial integrity of the composition; antioxidants; chelators and sequestrants; and aesthetic components such as fragrances, pigments, colorings, essential oils, and the like.

The composition can be formulated in a number of ways. In one method, a two vessel process is used. The water insoluble components are mixed together in one vessel, while the water soluble components are mixed in another. Heat is optionally applied to melt any solid components, a temperature of about 65° C. being suitable in most instances. The contents of the two vessels are then combined (preferably at the same temperature) and thoroughly mixed to provide an emulsion. Preferably, the antimicrobial agent is added at a temperature at which it is not subject to inactivation. For example, chlorhexidine salts are preferably added to the emulsion after cooling to below 50° C.

In another method, a single vessel is used. The water and other components, with the exception of the cyclomethicone (or other carrier oil) and antimicrobial agent, are heated in the vessel to a temperature slightly above, e.g., about 50° C. above, the highest melting temperature of the components present (typically approximately 65° C.) and mixed thoroughly. The mixture is then cooled to below about 50° C. and the cyclomethicone added and mixed with the other components. After mixing, the antimicrobial agent is added.

Other methods of combining the ingredients into an oil in water emulsion are also contemplated.

The composition may be dispensed from a bottle, tube, spray, wipe, or other suitable dispenser. Preferably, it is applied directly to the skin and rubbed in for few seconds to a minute. It may be applied neat or diluted, ether by hand or with a cloth or other applicator. The amount applied can vary although it is preferably applied in a pharmaceutically acceptable amount, i.e., one which is sufficient to achieve a desired level of antimicrobial activity and moisturizing effect without harmful results to the skin. The skin is decontaminated within about one minute. Leaving the composition on the skin allows continued moisturizing and antimicrobial effect for several hours or more. For example, the composition may be applied to a patients' skin up to about 12 hours before a surgical procedure is to take place.

The invention is further illustrated by the following examples, without intending to limit the scope of the invention.

EXAMPLES

Example 1

Formulation for Antimicrobial Lotion

An antimicrobial lotion which is fast acting yet moisturizing to the skin was prepared according to the formulation in TABLE 1. The concentration of the 20% chlorhexidine digluconate (CHG) solution and water was adjusted slightly, based on activity level of the CHG solution.

TABLE 1

| Ingredient | % | Function |
|---|---|---|
| Deionized Water | 71.065 | External phase |
| Steareth-2 | 0.595 | Nonionic Emulsifier |
| Steareth-100 | 0.540 | Nonionic emulsifier |
| Steareth-10 | 0.250 | Nonionic Emulsifier |
| Sodium lauroyl lactylate | 0.200 | Anionic Emulsifier/emollient |
| Dimethicone - 1000 centistokes, NF | 0.250 | Skin conditioner |
| Glycerine | 7.000 | Humectant |
| Emulsifying Wax, NF (cetostearyl alcohol) | 4.000 | Emulsifier/Emollient/Thickener |
| Cetyl alcohol | 0.500 | Emulsifier/Emollient/Thickener |
| Polyquaternium-7 | 0.500 | Skin Conditioner Emollient/Carrier/ |
| Cyclomethicone | 10.000 | Lubricity |
| Chlorhexidine digluconate (20%) | 5.0 (1.0% active) | Active ingredient-Antimicrobial |
| Fragrance | 0.100 | Fragrance |

A single vessel was used to prepare the composition. The water and other components, with the exception of the cyclomethicone and chlorhexidine digluconate, were heated in the vessel to a temperature of about 65° C. (i.e., above the highest melting temperature of the components present) and mixed thoroughly. The mixture was then cooled to below about 50° C. and the cyclomethicone added and mixed with the other components. After mixing, the chlorhexidine digluconate was added.

Example 2

Formulation for Antimicrobial Lotion

An antimicrobial lotion which is fast acting yet moisturizing to the skin was prepared according to the formulation in TABLE 2 using the method of EXAMPLE 1. The lotion had a higher level of chlorhexidine gluconate (1.5% CHG) than the lotion of Example 1 (1% CHG). The concentration of the 20% CHG solution and water was adjusted slightly, based on activity level of the CHG solution.

TABLE 2

| Ingredient | % | Function |
|---|---|---|
| Deionized Water | 73.925 | |
| Steareth-21 | 0.935 | Nonionic Emulsifier |
| Steareth-10 | 0.440 | Nonionic Emulsifier |
| Sodium lauroyl lactylate | 0.200 | Anionic Emulsifier/emollient |
| propylene glycol | 3.500 | Humectant |
| Cetyl alcohol | 3.000 | Emulsifier/Emollient Thickener |
| polyquaternium-7 | 0.500 | Skin Conditioner |
| Cyclomethicone | 10.000 | Emollient/Carrier/Lubricity |

TABLE 2-continued

| Ingredient | % | Function |
|---|---|---|
| Chlorhexidine digluconate (20%) | 7.50 (1.50% active) | Active |

Example 3

Formulation for Antimicrobial Lotion

An antimicrobial lotion was prepared according to the formulation in TABLE 3 using the method of EXAMPLE 1. The lotion had a higher level of chlorhexidine gluconate (1.5%) than the lotion of EXAMPLE 1. The concentration of the 20% CHG solution and water was adjusted slightly, based on activity level of the CHG solution.

TABLE 3

| Ingredient | % | Function |
|---|---|---|
| Deionized Water | 68.565 | External phase |
| Steareth-2 | 0.595 | Nonionic Emulsifier |
| Steareth-100 | 0.540 | Nonionic emulsifier |
| Steareth-10 | 0.250 | Nonionic Emulsifier |
| Sodium lauroyl lactylate | 0.200 | Anionic Emulsifier/emollient |
| Dimethicone - 1000 centistokes, NF | 0.250 | Skin conditioner |
| Glycerine | 7.000 | Humectant |
| Emulsifying Wax, NF (cetostearyl alcohol) | 4.000 | Emulsifier/Emollient/Thickener |
| Cetyl alcohol | 0.500 | Emulsifier/Emollient/Thickener |
| Polyquaternium | 0.500 | Skin Conditioner |
| Cyclomethicone | 10.000 | Emollient/Carrier/Lubricity |
| Fragrance | 0.100 | Fragrance |
| Chlorhexidine digluconate (20%) | 7.5% (1.5% active) | Active |

Example 4

Results for Healthcare Personnel Handwash Clinical Study (*Serratia marcescens* ATCC 14756)

The products of Examples 1–3 were tested according to ASTM method E 11747. The results were compared with those for a commercial chlorhexidine digluconate skin wash formulation, Hibiclens™. The test involved applying 5ml of a bacterial suspension of *Serratia marcescens* to the skin and then applying the selected lotion or wash product. In the case of the lotions of Examples 1–3, the lotion was applied to the skin and rubbed for 90 seconds, prior to conducting the first wash (a 15 second rinse under water). In normal use, the lotions would typically be left on the skin for longer times prior to washing. In the case of the Hibiclens, the label instructions for application were followed. These call for a 15 second application period, in which the product was rubbed into the skin, followed by a 15 second rinse under water. TABLE 4 compares the results after several washes, with n being the number of subjects tested. The results are expressed as log reductions from the baseline value (initial value), a log reduction of 1 indicating a 90% reduction in viable microorganisms and a log reduction of 6 indicating only 1 viable microorganism out of every million microorganisms remains.

TABLE 4

| Product | n | Wash 1 | Wash 3 | Wash 7 | Wash 10 |
| --- | --- | --- | --- | --- | --- |
| Example 1 | 6 | 2.66 | 3.46 | 3.78 | 4.18 |
| Example 2 | 6 | 3.80 | 5.10 | 5.61 | 5.54 |
| Example 3 | 6 | 4.00 | 4.91 | 5.17 | 5.60 |
| Hibiclens (4% CHG) | 6 | 3.90 | 3.43 | 3.88 | 3.99 |

The results show that for the products of EXAMPLES 1 to 3, efficacy increases with percentage concentration of CHG (higher log reductions). However, all of the products performed as well as, or better than the 4% wash product (Hibiclens), even when the amount of CHG was only 1%. This shows that effective lotions which retain their efficacy after repeated washes can be prepared without the need for high concentrations of antimicrobial.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A fast acting antimicrobial lotion comprising, as a percent by weight:
   0.25–8.0% of a nonionic emulsifier;
   0.1–2.0% of an anionic emulsifier which includes a cationic salt of an ester of lactyl lactylate;
   0.5–10.0% of a thickener;
   0–15.0% of a humectant;
   0.02–5.0% of a skin conditioner;
   2.0–20.0% of an oil;
   0.25–5% of a cationic antimicrobial agent selected from the group consisting of salts of chlorhexidine, benzalkonium chloride, benzethonium chloride, polyhexamethylene biguanide, and combinations thereof; and
   water.

2. The antimicrobial lotion of claim 1, wherein:
   the nonionic emulsifier is selected from the group consisting of polyoxyethylene alcohols and glycol fatty acid esters with an ethoxylation range of 2–100 mols, fatty acid esters of sorbitan and polyoxyethylene sorbitan, polyoxyethylene fatty acid esters, quaternary amine salts of fatty acids, phospholipid complexes polyol fatty acid esters, polymeric surfactants, and combinations thereof.

3. The antimicrobial lotion of claim 2, wherein the nonionic emulsifier includes a $C_{12}$–$C_{22}$ ethoxylated fatty alcohol.

4. The antimicrobial lotion of claim 3, wherein the the nonionic emulsifier includes at least one steareth compound.

5. The antimicrobial lotion of claim 1, wherein the lactyl lactylate is selected from the group consisting of caproyl, isostearoyl, cocoyl, hydroxystearoyl, behenoyl, stearoyl, and lauroyl lactylates.

6. The antimicrobial lotion of claim 1, wherein the lactyl lactylate includes sodium lauroyl lactylate.

7. The antimicrobial lotion of claim 1, wherein the anionic and nonionic emulsifiers are at a concentration which maintains the cationic antimicrobial agent primarily in the water phase.

8. The antimicrobial lotion of claim 1, wherein the cationic antimicrobial agent includes a salt of chlorhexidine.

9. The antimicrobial lotion of claim 8, wherein the salt of chlorhexidine is selected from the group consisting of chlorhexidene digluconate, chlorhexidene acetate, chlorhexidene isethionate, chlorhexidene hydrochloride, and combinations thereof.

10. The antimicrobial lotion of claim 9, wherein the salt of chlorhexidine includes chlorhexidene digluconate.

11. The antimicrobial lotion of claim 9, wherein the ratio of chlorhexidine digluconate:nonionic emulsifier is from about 1:5 to about 1:1.

12. The antimicrobial lotion of claim 1, wherein the thickener is selected from the group consisting of alcohols, emulsifying waxes, fatty acid esters, polymeric thickeners, polyethylene glycols, and combinations thereof.

13. The antimicrobial lotion of claim 12, wherein the thickener includes a fatty alcohol.

14. The antimicrobial lotion of claim 13, wherein the fatty alcohol includes cetyl alcohol.

15. The antimicrobial lotion of claim 1, wherein the humectant is present in the composition at a concentration of from 2–15% by weight.

16. The antimicrobial lotion of claim 15, wherein the humectant is selected from the group consisting of polyhydric alcohols, polyethylene glycols, lower alcohols, triglycerides, ethyl acetate, acetone, triacetin, and combinations thereof.

17. The antimicrobial lotion of claim 16, wherein the humectant includes a polyhydric alcohol.

18. The antimicrobial lotion of claim 1, wherein the skin conditioner is selected from the group consisting of quaternary ammonium salts, nonvolatile silicones, hydroxy-terminated dimethyl silicones, silicone polyethers, alkyl methyl silicones, $C_8$–$C_{30}$ alkyl esters of $C_8$–$C_{30}$ carboxylic acids, $C_1$–$C_6$ diol monoesters and diesters of $C_8$–$C_{30}$ carboxylic acids, cholesterol esters of $C_8$–$C_{30}$ carboxylic acids, monoglycerides, diglycerides, and triglycerides of $C_8$–$C_{30}$ carboxylic acids, polyethylene glycol derivatives of vegetable glycerides, hydrocarbon oils or waxes, silicone gum/resin blends, and combinations thereof.

19. The antimicrobial lotion of claim 18, wherein the skin conditioner is selected from the group consisting of polyquaternium compounds dimethicone, dimethiconol, cetyl esters, glyceryl esters of fatty acids, palm kernel glyceride, caprylic glyceride, and capric glyceride, glyceryl cocoate, $C_{12}$–$C_{15}$ alkyl berzoates, dipropylene glycol benzoate, PPG 15 stearyl ether benzoate, chitosan, cetyl lactate, and combinations thereof.

20. The antimicrobial lotion of claim 19, wherein the skin conditioner includes a polyquaternium compound.

21. The antimicrobial lotion of claim 1, wherein the oil is selected from the group consisting of volatile silicones and siloxanes.

22. The antimicrobial lotion of claim 21, wherein the oil includes cyclomethicone.

23. The antimicrobial lotion of claim 1, wherein:
   the nonionic emulsifier includes at least one steareth compound;
   the thickener includes a fatty alcohol;
   the humectant includes a polyhydric alcohol;
   the skin conditioner includes a polyquaternium compound;
   the oil includes cyclomethicone; and
   the antimicrobial agent includes chlorhexidine digluconate.

24. The antimicrobial lotion of claim 23, wherein:
   the steareth compound is present at a concentration of 1.0–5.0 weight percent;

the lactylate is present at a concentration of 0.1–0.75 weight percent;

the fatty alcohol is present at a concentration of 0.5–6.0 weight percent;

the polyhydric alcohol is present at a concentration of 2.0–10.0 weight percent;

the polyquaternium compound is present at a concentration of 0.02–2.0 weight percent;

the cyclomethicone is present at a concentration of 5.0–12.0 weight percent; and the chlorhexidine digluconate is present at a concentration of 0.5–4.0 weight percent.

25. The antimicrobial lotion of claim 1, wherein the lactyl lactylate of the general formula $RCO(OCHCH_3CO)_n\ O^-\ X^+$, where:

R is a long chain aliphatic group, n is an integer, and

X is a cation.

26. An antimicrobial lotion comprising, as a percent by weight:

0.25–8.0of a nonionic emulsifier;

0.1–2.0% of an anionic emulsifier which includes a cationic salt of an ester of a lactylate selected from the group consisting of lauroyl lactylate, caproyl lactylate, stearoyl lactylate, isostearoyl lactylate, cocoyl lactylate, hydroxystearoyl lactylate, behenoyl lactylate, and combinations thereof;

0.5–10.0% of a thickener;

0–15.0% of a humectant;

0.02–5.0% of a skin conditioner;

2.0–20.0% of an oil;

0.25–5% of a cationic antimicrobial agent selected from the group consisting of salts of chlorhexidine, benzalkonium chloride, benzethonium chloride, polyhexamethylene biguanide, and combinations thereof; and water.

27. A method of antimicrobially decontaminating and moisturizing the skin comprising:

applying to the skin a pharmaceutically effective amount of a lotion which includes:

0.25–8.0% of a nonionic emulsifier;

0.1–2.0% of an anionic emulsifier which includes a cationic salt of an ester of lactyl lactylate;

0.5–10.0% of a thickener;

0–15.0% of a humectant;

0.02–5.0% of a skin conditioner;

2.0–20.0% of an oil;

0.2–5% of a cationic antimicrobial agent selected from the group consisting of salts of chlorhexidine, benzalkonium chloride, benzethonium chloride, polyhexamethylene biguanide, and combinations thereof; and water.

* * * * *